(12) United States Patent
Eckert et al.

(10) Patent No.: US 9,173,820 B2
(45) Date of Patent: Nov. 3, 2015

(54) DENTAL COMPOSITION, METHOD OF PRODUCING AND USE THEREOF

(75) Inventors: Adrian S. Eckert, Herrsching (DE); Christoph Thalacker, Weilheim (DE); Karsten Dede, Landsberg (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/237,210

(22) PCT Filed: Aug. 10, 2012

(86) PCT No.: PCT/US2012/050331
§ 371 (c)(1),
(2), (4) Date: Feb. 5, 2014

(87) PCT Pub. No.: WO2013/023138
PCT Pub. Date: Feb. 14, 2013

(65) Prior Publication Data
US 2014/0200284 A1    Jul. 17, 2014

(30) Foreign Application Priority Data

Aug. 11, 2011  (EP) .................................... 11177273

(51) Int. Cl.
*A61K 6/00*     (2006.01)
*A61K 6/083*    (2006.01)
*A61K 6/09*     (2006.01)

(52) U.S. Cl.
CPC ............... *A61K 6/0023* (2013.01); *A61K 6/083* (2013.01); *A61K 6/09* (2013.01)

(58) Field of Classification Search
CPC ........ C08K 6/083; C08K 6/09; C08K 6/0052; C08L 75/16
USPC ...................................................... 523/116
See application file for complete search history.

(56) References Cited

U.S. PATENT DOCUMENTS

| | | | |
|---|---|---|---|
| 3,347,954 A | 10/1967 | Hellmut | |
| 3,541,068 A | 11/1970 | Taylor | |
| 3,729,313 A | 4/1973 | Smith | |
| 3,741,769 A | 6/1973 | Smith | |
| 3,808,006 A | 4/1974 | Smith | |
| 4,071,424 A | 1/1978 | Dart | |
| 4,250,053 A | 2/1981 | Smith | |
| 4,394,403 A | 7/1983 | Smith | |
| 4,544,742 A | 10/1985 | Schmitt | |
| 4,642,126 A | 2/1987 | Zador | |
| 4,652,274 A | 3/1987 | Boettcher | |
| 4,737,593 A | 4/1988 | Ellrich | |
| 4,744,827 A | 5/1988 | Winkel | |
| 4,744,828 A | 5/1988 | Winkel | |
| 4,772,530 A | 9/1988 | Gottschalk | |
| 4,874,450 A | 10/1989 | Gottschalk | |
| 4,954,414 A | 9/1990 | Adair | |
| 5,055,372 A | 10/1991 | Shanklin | |
| 5,057,393 A | 10/1991 | Shanklin | |
| 5,332,429 A | 7/1994 | Mitra | |
| 5,545,676 A | 8/1996 | Palazzotto | |
| 5,624,260 A | 4/1997 | Wilcox | |
| 5,865,803 A | 2/1999 | Major | |
| 5,893,714 A | 4/1999 | Arnold | |
| 5,918,772 A | 7/1999 | Keller | |
| 5,944,419 A | 8/1999 | Streiff | |
| 6,572,693 B1 | 6/2003 | Wu | |
| 6,899,948 B2 | 5/2005 | Zhang | |
| 7,601,767 B2 | 10/2009 | Ruppert | |
| 2003/0008967 A1 | 1/2003 | Hecht | |
| 2006/0187752 A1 | 8/2006 | Keller | |
| 2007/0090079 A1 | 4/2007 | Keller | |
| 2007/0172789 A1 | 7/2007 | Muller | |
| 2008/0167399 A1 | 7/2008 | Utterodt | |
| 2009/0036565 A1 | 2/2009 | Utterodt | |
| 2012/0082958 A1* | 4/2012 | Blomker et al. | 433/219 |

FOREIGN PATENT DOCUMENTS

| | | |
|---|---|---|
| EP | 0595451 | 5/1994 |
| EP | 1340472 | 9/2003 |
| EP | 2008636 | 12/2008 |
| JP | 10-45702 | 2/1998 |
| WO | WO 2009-151957 | 12/2009 |

OTHER PUBLICATIONS

Sakaguchi, "Analysis of strain gage method for measurement of post-gel shrinkage in resin composites", Dental Material, Jul. 1997, vol. 13, No. 4, pp. 233-239.
Watts, "Determination of polymerization shrinkage kinetics in visible-light-cured materials: methods development", Dental Materials, Oct. 1991, vol. 7, No. 4, pp. 281-287.
International Search Report for PCT International Application No. PCT/US2012/050331 Mailed on Nov. 22, 2012, 4 pages.

\* cited by examiner

Primary Examiner — Tae H Yoon

(57) ABSTRACT

The invention is directed to a composition comprising a) compound (A) being characterized by at least the following features: comprising a backbone unit (U) comprising a tricyclic hydrocarbon moiety, two spacer units (S) each comprising a hydrocarbon chain (G) being directly connected to the backbone unit (U) via an urethane moiety, and at least two reactive groups (M) being connected to the hydrocarbon chain (G) via an ester linkage, with (G) being a non-branched hydrocarbon chain having a length of at least 3 carbon atoms, (G) not comprising ether moieties, and (M) being selected from acroyl and methacroyl, b) initiator (B) and c) optionally filler (C), the composition being a dental composition.

15 Claims, No Drawings

DENTAL COMPOSITION, METHOD OF PRODUCING AND USE THEREOF

CROSS REFERENCE TO RELATED APPLICATIONS

This application is a national stage filing under 35 U.S.C. 371 of PCT/US2012/050331, filed Aug. 10, 2012, which claims priority to European Application No. 11177273.7, filed Aug. 11, 2011, the disclosures of which are incorporated by reference in their entirety herein.

FIELD OF THE INVENTION

The invention relates to a composition comprising a hardenable compound, which contains a comparable rigid backbone unit, a spacer unit and a unit comprising polymerizable endgroups being connected to the spacer unit via urethane moieties.

This composition is useful in the dental field and in particular for providing so-called low-stress composite filing materials.

BACKGROUND ART

Volume shrinkage of curable compositions during the curing process is known since a long time. Especially, in the dental area, this can cause problems as e.g. a gap might be formed between the cured composition and the wall of the tooth cavity. This might lead to an infection of the remaining tooth structure. Various attempts were undertaken to address this problem.

US 2009/0036565 relates to dental composites based on (meth)acrylates, exhibiting a proportion of TCD (i.e. tricyclo [5.2.1.0$^{2,6}$]decane-3/4,8/9-diyl) derived monomers, wherein the quotient of flexural strength/shrinkage tension is at least 35.

US 2008/0167399 relates to dental composites comprising a crosslinking agent formed from acrylates and a certain TCD urethane structure.

U.S. Pat. No. 7,601,767 B2 relates to a composite material containing i.a. a monomer component comprising a mixture of Bis-GMA or TCD-di-HEMA or TCD-DiHEA, UDMA and TEDMA.

U.S. Pat. No. 4,744,827 relates to certain (meth)acrylate acid derivatives of tricyclodecanes comprising a X—Y—O—CO—C(R5)=CH2 unit with X being a divalent bridge member from the group —O—CO—NH— and —N(R6)-CO—NH— and Y denoting a certain divalent bridge member.

U.S. Pat. No. 4,744,828 describes (meth)acrylic acid derivatives of tricyclodecanes which may comprise one or two units having the formula —X—Y—CO—CR5-CH=CH2, with X being a divalent bridge comprising the group —NH—CO—O— or NH—CO—NR6- and Y being a linear or branched hydrocarbon chain which has 2 to 10 carbon atoms.

However, there is still room for improvement especially with regard to the requirements to be fulfilled with respect to modern dental materials.

Thus, there is still a need for an improved dental composition, which can be used inter alia as a restorative or temporary or long term crown and bridge material.

DESCRIPTION OF THE INVENTION

An object which can be addressed by the invention is the provision of a composition having advantageous properties e.g. with respect to shrinkage stress which may negatively influence the bonding behaviour of the composition to the surface of a prepared tooth (e.g. cavity walls of a preparation).

Moreover, another object which can be addressed by the invention is the provision of a composition which can be cured in a sufficient layer thickness thereby maintaining acceptable mechanical properties.

In one embodiment the present invention features a composition comprising
a) compound (A) being characterized by at least the following features:
  comprising a backbone unit (U) comprising a tricyclic hydrocarbon moiety (e.g. a TCD moiety),
  two spacer units (S) each comprising a hydrocarbon chain (G) being directly connected to the backbone unit (U) via an urethane moiety, and
  at least two reactive groups (M) being connected to the hydrocarbon chain (G) via an ester linkage,
  with
  (G) being a non-branched hydrocarbon chain having a length of at least 3 carbon atoms, (G) not comprising ether moieties, and
  (M) being selected from acroyl and methacroyl,
b) initiator (B) and
c) optionally filler (C),
the composition being a dental composition or is to be used in the dental field.

The invention also relates to a process of producing the composition comprising a mixing step.

According to another embodiment, the invention relates to the use of the composition as described in the text of the invention for producing a dental cement, a crown and bridge material, a dental filling material, a casting material, a cavity liner, a coating composition, a mill blank, an orthodontic devices, a sealant or combinations thereof.

The invention is also directed to a kit or parts comprising at least 2 compositions as described in the text of the invention, the compositions differ from each other at least with respect to their colour.

If desired, the composition described in the present text can be placed in contact with a surface, e.g. the surface of a dental tooth and subsequently hardened.

DEFINITIONS

Within the description of the invention, the following terms are defined as follows:

The term "visible light" is used to refer to light having a wavelength of about 400 to about 800 nanometers (nm).

A "dental composition" is any composition which can be used in the dental field. In this respect the composition should be not detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices.

Dental compositions are typically hardenable compositions, which can be hardened at ambient conditions, including a temperature range from about 15 to 50° C. or from about 20 to 40° C. within a time frame of about 30 min or 20 min or 10 min.

Higher temperatures are not recommended as they might cause pain to the patient and may be detrimental to the patient's health.

Dental compositions are typically provided to the practitioner in comparable small volumes, that is volumes in the range from about 0.1 to about 100 ml or from about 0.5 to about 50 ml or from about 1 to about 30 ml.

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

A "hardenable compound or material" is any compound which can be cured or solidified e.g. by heating to cause polymerization, chemical crosslinking, radiation-induced polymerization or crosslinking or using a redox initiator. A hardenable compound may contain only one, two, three or more polymerizable groups. Typical examples of polymerizable groups include epoxy groups and unsaturated carbon groups, such as a vinyl group being present i.a. in a (methyl) acrylate group.

A "resin" contains the hardenable compounds (monomers, oligomers and/or polymers) being present in the hardenable composition. The resin may contain only one hardenable compound or a mixture of different hardenable compounds.

A "filler" contains all fillers being present in the hardenable composition. Only one type of filler or a mixture of different fillers can be used.

"Dispersed within the resin" means that filler particles are present in the resin as discrete, unassociated (i.e. non-agglomerated and non-aggregated) particles.

A "nano-sized filler" is a filler, the individual particles thereof have a size in the region of nanometers, e.g. an average particle diameter of less than about 200 nm. Useful examples are given in U.S. Pat. No. 6,899,948 and U.S. Pat. No. 6,572,693, the content of which especially with regard to nano-sized silica particles is herein incorporated by reference.

An "initiator or initiator system" is a substance being able to start the curing process of a hardenable compound.

A "curing, hardening or setting reaction" is used interchangeable and refers to a reaction wherein physical properties such as viscosity and hardness of a composition changes over the time due to a chemical reaction between the individual components.

A "derivative" is a chemical compound showing a chemical structure closely related to the corresponding reference compound and containing all featured structural elements of the corresponding reference compound but having small modifications like bearing in addition comparably small additional chemical groups like e.g. $CH_3$, Br, Cl, or F or not bearing comparably small chemical groups like e.g. $CH_3$ in comparison to the corresponding reference compound. The following examples might illustrate this: tetramethyl bis-phenol A bearing four additional methyl groups with respect to the reference compound bis-phenol A, and bis-phenol F not bearing two additional methyl groups with respect to the reference compound bis-phenol A are derivatives of bis-phenol A within the meaning of this definition.

An "urethane moiety" has the structural element —NH—CO—O—. The urethane moiety is connected to other moieties through the nitrogen and the oxygen (of the urethane moiety). Depending on the orientation of the connection, the physical properties of the resulting molecule may differ.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about."

DETAILED DESCRIPTION OF THE INVENTION

The inventive composition is beneficial for the dentist in a couple of aspects.

E.g., it was found that compound (A) being contained in the inventive composition contributes to at least one or more of the following properties:
   a) Compound (A) typically has a good filler/pigment wettability (e.g. useful to achieve comparably high filler loads),
   b) Compound (A) typically has a comparably high hydrophobicity (e.g. useful to achieve comparably low water uptake and/or exogenic staining),
   c) Compound (A) can be used to provide compositions showing low shrinkage stress during or after curing (e.g. useful for avoiding post-op sensitivity and ensuring long-term marginal integrity),
   d) Compound (A) can be used to provide compositions showing high depth of cure (e.g. useful for bulk cure applications, if desired),
   e) Compound (A) can be used to provide compositions with appropriate mechanical properties (i.e. a comparably high flexural strength; e.g. useful for comparably high durability),
   f) Compound (A) typically shows a medium E-Modulus at standard wear resistance (measured according to ACTA; e.g. useful for comparably low brittleness),
   g) Compound (A) typically has a viscosity which facilitates the production process for the composition, e.g. in that a high filler load can be incorporated, if desired. Moreover, the final composition is typically easy to handle, e.g. it can be applied to surfaces in thin sheets without showing disruptions.

One or more of these properties can be obtained by using a compound having a comparable rigid backbone unit, a flexible spacer unit of a certain length and urethane units.

The combination of the properties low shrinkage stress, high depth of cure, appropriate mechanical properties and medium E-Modulus has been proven to beneficial, especially in the dental area.

Without wishing to be bound to a certain theory, it is believed that the presence of urethane units contributes to the formation of a secondary network due to their ability of forming hydrogen bonds.

Moreover, it is assumed that the nature and length of the spacer units contribute to influence the viscosity of the compound.

The rigid backbone containing a tricyclic hydrocarbon moiety may contribute to the hydrophobicity.

Thus, compound (A) shows a unique combination of features which help to provide a dental composition having advantageous properties, especially showing low stress during hardening.

Compound (A) can be characterized by the following features.

comprising a backbone unit (U) comprising a tricyclic hydrocarbon moiety (e.g. a tricyclodecane moiety), comprising two spacer units (S) each comprising a hydrocarbon chain (G) which is directly connected to the backbone unit (U) via an urethane moiety, especially wherein the urethane moiety is connected to the backbone unit (U) through the oxygen moiety (i.e. compound (A) comprises the structural element —NH—CO—O—(U)—O—CO—NH—), comprising at least two reactive groups (M) being connected to the hydrocarbon chain (G) via an ester linkage, with (G) being a non-branched hydrocarbon chain having a length of at least 3 carbon atoms, (G) not comprising ether moieties, and (M) being selected from acroyl and methacroyl.

Examples of the tricyclic hydrocarbon moiety include the so-called TCD alcohol (i.e. 3/4,8/9-tricyclo[5.2.1.0$^{2,6}$]decane-dimethanole) and derivatives thereof (e.g. structures comprising C1 to C4 alkyl substituents).

Examples of the non-branched hydrocarbon chain (G) include C3 to C12 or C3 to C8 alkylene moieties, e.g. —CH2-CH2-CH2-(C3), —CH2-CH2-CH2-CH2-(C4), —CH2-CH2-CH2-CH2-CH2-(C5), —CH2-CH2-CH2-CH2-CH2-CH2-(C6), —CH2-CH2-CH2-CH2-CH2-CH2-CH2-(C7) and —CH2-CH2-CH2-CH2-CH2-CH2-CH2-CH2-(C8).

Without wishing to be bound to a certain theory it is believed that the presence of two hydrocarbon chains being a) non-branched and b) having a certain length contributes to the lowering of the viscosity of the molecule.

Also the orientation of the urethane moieties within compound (A) may influence the viscosity of compound (A), e.g. by enhancing or decreasing the ability of the molecule to form hydrogen bridges. Molecules wherein the urethane moiety is connected to the backbone unit (U) through the oxygen were found to be particular useful.

Compound (A) does typically not comprise moieties like epoxy, bisphenol, halogen and combinations thereof.

Components comprising a bisphenol moiety include bisphenol A, bisphenol AP (4,4'-(1-Phenylethylidene)bisphenol), bisphenol C (Bis(4-hydroxyphenyl)-2,2-dichloroethylene), bisphenol F (Bis(2-Hydroxyphenyl)methane), bisphenol TMC (4,4'-(3,3,5-Trimethylcyclohexylidene)bisphenol). These and other abbreviations are known to the person skilled in the art.

If desired, different compounds falling within the definition of compound (A) can be present in the composition. E.g. the inventive composition may contain two, three, four or even more compounds, which differ from each other e.g. by the nature of the backbone unit and/or the nature of the spacer unit(s).

According to one embodiment compound (A) can be characterized by at least one of the following features:
a) Molecular weight (Mw): from about 500 to about 600,
b) Functionality: only 2 reactive (e.g. hardenable) moieties per molecule;
c) Number of urethane moieties: only 2;
d) Number of ester moieties: only 2;
e) Viscosity: below about 200 Pa*s or below about 150 Pa*s (measured at 23° C.).

Particular examples of compound (A) include:

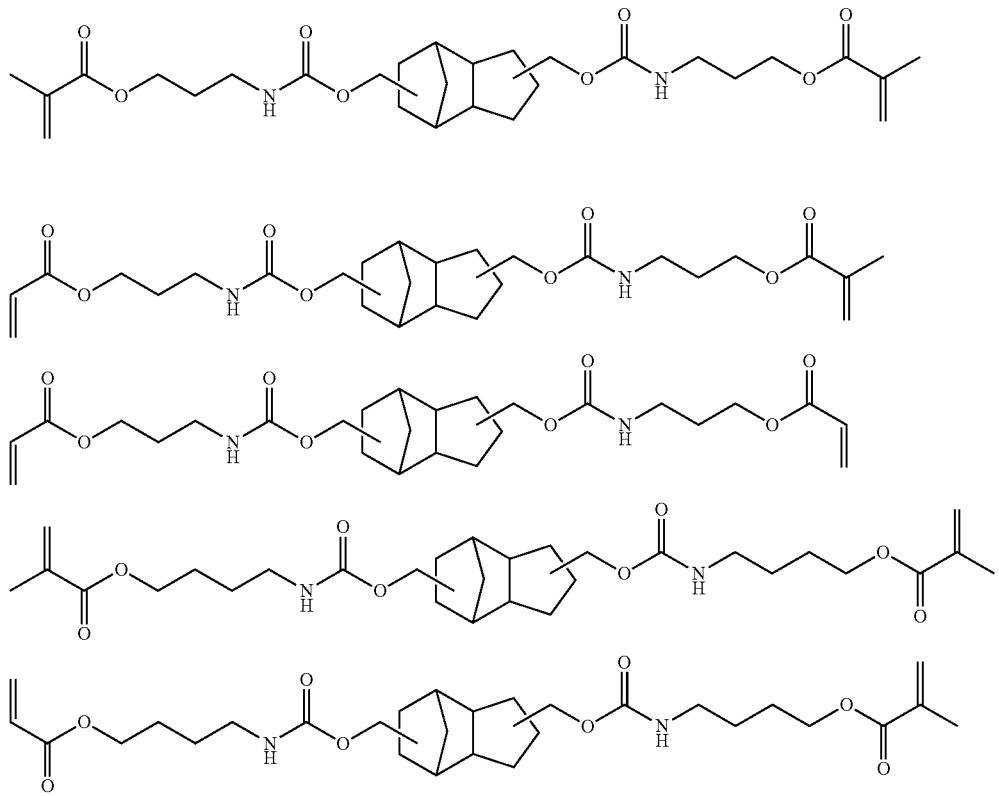

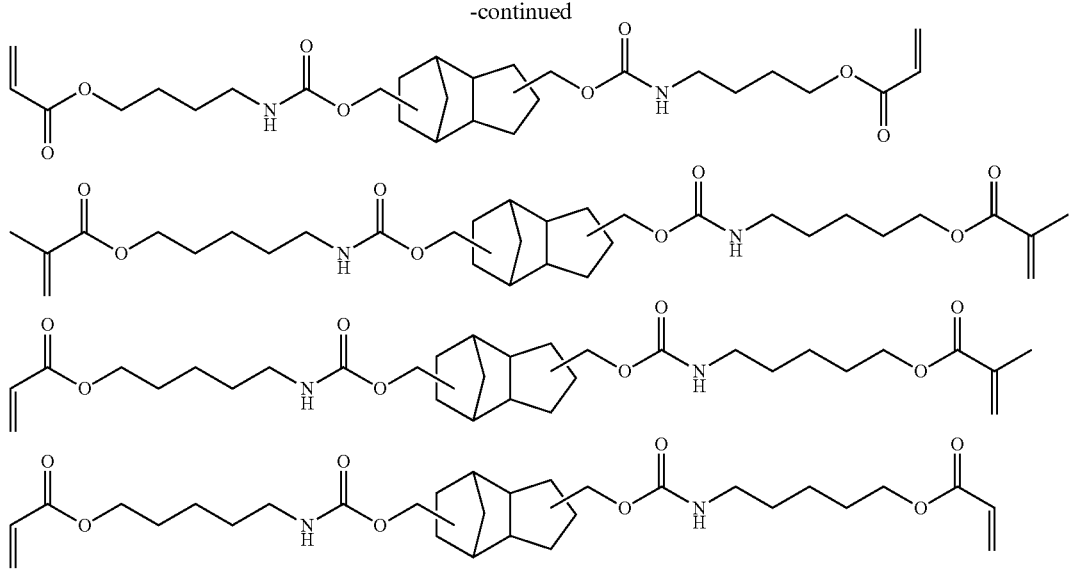

and mixtures thereof.

Compound (A) is typically present in the composition in an amount of at least about 5 wt.-% or at least about 10 wt.-% or at least about 20 wt.-% with respect to the weight of the whole composition.

The amount of compound (A) contained in the composition is typically up to about 50 wt.-% or up to about 60 wt.-% or up to about 70 wt.-% with respect to the weight of the whole composition.

Typical ranges include from about 5 to about 70 or from about 10 to about 60 or from about 10 to about 45 or from about 10 to about 30 wt.-% with respect to the weight of the whole composition.

The inventive dental composition also comprises an initiator or initiator system being able to start the curing process of the hardenable components being present in the resin matrix.

Dental materials of the invention can be chemically curable, heat curable or light curable compositions. Light curable materials should have an appropriate initiator system. Chemically curable materials can be auto-cured (e.g. via redox initiators). Alternatively, the materials of the invention can be hardened by a combination of auto- and light-cure.

For free radical polymerization (hardening), an initiation system can be selected from systems which initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between about 200 and about 800 nm.

A variety of visible or near-IR photoinitiator systems may be used for photopolymerization of free-radically polymerizable materials useful in the invention. For example, in free radical polymerization (hardening), a photoinitiation system can be selected from systems which initiate polymerization via a two component system of an amine and an α-diketone as described in U.S. Pat. No. 4,071,424 and WO 2009151957, which are herein incorporated by reference. Alternatively, the resin can be combined with a three components or ternary photoinitiator system such as described in U.S. Pat. No. 5,545,676 and WO 2009151957, which are incorporated herein by reference.

In the ternary photoinitator system, the first component is an iodonium salt, i.e., a diaryliodonium salt. The iodonium salt is preferably soluble in the monomer and shelf-stable (i.e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. No. 3,729,313, U.S. Pat. No. 3,741,769, U.S. Pat. No. 3,808,006, U.S. Pat. No. 4,250,053 and U.S. Pat. No. 4,394,403, the iodonium salt disclosures of which are incorporated herein by reference. The iodonium salt can be a simple salt (e.g., containing an anion such as $Cl^-$, $Br^-$, $I^-$ or $C_4H_5SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing a julolidinyl moiety. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption at the excitation wavelength upon irradiation can be used.

For example, a preferred class of ketone sensitizers has the formula: $ACO(X)_bB$, where X is CO or $CR^5R^6$, where $R^5$ and $R^6$ can be the same or different, and can be hydrogen, alkyl, alkaryl or aralkyl, b is zero or one, and A and B different and can be substituted (having one or more non-interfering substituents) can be the same or or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incorporated herein by reference.

Alternatively, free-radical initiators useful in the invention include the class of acylphosphine oxides, as described in U.S. Pat. No. 4,737,593. Such acylphosphine oxides are of the general formula

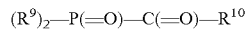

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Preferred acylphosphine oxides useful in the invention are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE™ 819, Ciba Specialty Chemicals, Tarrytown, N.Y.).

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis(η5-2,4-cyclopentadien-1-yl)-bis(2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Another free-radical initiator system that can alternatively be used in the dental materials of the invention includes the class of ionic dye counterion complex initiators comprising a borate anion and a complementary cationic dye.

Borate salt photoinitiators are described, for example, in U.S. Pat. No. 4,772,530, U.S. Pat. No. 4,954,414, U.S. Pat. No. 4,874,450, U.S. Pat. No. 5,055,372, and U.S. Pat. No. 5,057,393, the disclosures of which are incorporated herein by reference.

Borate anions useful in these photoinitiators generally can be of the formula $R^1R^2R^3R^4B^-$, wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium.

Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands.

Yet another alternative class of initiators capable of initiating polymerization of free radically active functional groups includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. to 15° C. under normal conditions or at elevated pressure. This procedure is preferred for initiating polymerization of materials occurring outside of the oral environment.

Organic peroxide compounds together with so-called activators are also suitable as redox initiator systems. In particular, compounds such as lauroyl peroxide, benzoyl peroxide and p-chlorobenzoyl peroxide and p-methylbenzoyl peroxide can be considered as organic peroxide compounds.

Suitable as activators are, for example, tertiary aromatic amines, such as the N,N-bis-(hydroxyalkyl)-3,5-xylidines known from U.S. Pat. No. 3,541,068 as well as N,N-bis-(hydroxyalkyl)-3,5-di-t-butylanilines, in particular N,N-bis-([beta]-oxybutyl)-3,5-di-t-butylaniline as well as N,N-bis-(hydroxyalkyl)-3,4,5-trimethylaniline.

Well-suited activators are also the barbituric acids and barbituric acid derivatives as described in US 2003/008967, DE 14 95 520 as well as the malonyl sulfamides described in U.S. Pat. No. 4,544,742 (corresponding to EP 0 059 451). Preferred malonyl sulfamides are 2,6-dimethyl-4-isobutyl-malonyl sulfamide, 2,6-diisobutyl-4-propylmalonyl sulfamide, 2,6-dibutyl4-propylmalonyl sulfamide, 2,6-dimethyl4-ethylmalonyl sulfamide and 2,6-dioctyl4-isobutyl malonyl sulfamide.

For further acceleration, the polymerization is in this case preferably carried out in the presence of heavy-metal compounds and ionogenic halogen or pseudohalogen. The heavy metal is suitably used in the form of soluble organic compounds. Likewise, the halide and pseudohalide ions are suitably used in the form of soluble salts, as examples there can be named the soluble amine hydrochlorides as well as quarternary ammonium chloride compounds. Suitable accelerators are in particular metals from the iron or copper group, preferably copper and iron complexes and in particular copper complexes. The heavy metal is preferably employed in the form of soluble organic compounds. Suitable are, for example, iron carboxylates, copper carboxylates, iron procetonate, copper procetonate, copper naphthenate, copper acetate and iron naphthenate.

The initiator is typically present in the composition in an amount of at least about 0.1 wt.-% or at least about 0.2 wt.-% or at least about 0.3 wt.-%.

The amount of initiator contained in the composition is typically up to about 3 wt.-% or up to about 2 wt.-% or up to about 1.8 wt.-%.

Typical ranges include from about 0.1 to about 3 or from about 0.2 to about 2 or from about 0.3 to about 1.8 wt.-%.

The inventive composition may comprise a filler or a filler matrix. The filler matrix can be comprised of one filler or a mixture of different fillers.

The nature of filler of the inventive composition is not particularly limited. The size of the filler particles should be such that a homogeneous mixture with the hardenable component(s) forming the resin matrix can be obtained.

Useful fillers include fumed silica, fillers based on fluoroaluminosilicate glasses, quartz, ground glasses, non-water-soluble fluorides such as $CaF_2$, silica gels such as silicic acid, in particular pyrogenic silicic acid and granulates thereof, cristobalite, calcium silicate, zirconium silicate, zeolites, including the molecular sieves, metal oxide powders, such as aluminium or zinc oxides or their mixed oxides, barium sulphate, yttrium fluoride, calcium carbonate.

The silica is usually dispersed within the resin matrix. The silica particles used in the dental compositions of the invention preferably have an average diameter of less than about 200 nm; more preferably, the particles are less than about 100 nm in average diameter. These measurements are preferably based on a TEM (transmission electron microscopy) method, whereby a population is analyzed to obtain an average particle diameter. A preferred method for measuring the particle diameter can be described is as follows:

Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50-100 particles can be measured and an average diameter is determined.

The average surface area of the silica particles is preferably greater than about 15 $m^2/g$ more preferably greater than about 30 $m^2/g$.

Once dispersed in the resin, the silica particles are in a discrete (individual) and unassociated (i.e. non-agglomerated, non-aggregated) condition. "Agglomerated" as used herein, is descriptive of a weak association of particles usually held together by charge or polarity and can be broken down into smaller entities. "Aggregated," as used herein, is descriptive of a strong association of particles often bound together by, for example, residual chemicals treatment; further breakdown of the aggregates into smaller entities is very difficult to achieve.

The silica particles which can be used in the dental materials of the invention are preferably substantially spherical and substantially non-porous. Although the silica is preferably essentially pure, it may contain small amounts of stabilizing ion such as ammonium and alkaline metal ions.

Suitable fumed silicas include for example, products sold under the tradename AEROSIL series OX-50, -130, -150, and -200 available from Degussa AG, (Hanau, Germany), and CAB-O-SIL M5 available from Cabot Corp (Tuscola, Ill.).

Useful fluoroaluminosilicate glasses include silanol treated fluoroaluminosilicate glass fillers, as described in U.S. Pat. No. 5,332,429, the disclosure of which is expressly incorporated by reference herein. For example, a fluoride releasing glass may be added to the dental composition to provide the benefit of long-term release of fluoride in use, for example in the oral cavity.

Optionally, a heavy metal oxide can be included in the dental materials of the invention to provide a radiopaque dental material. It is preferred that the heavy metal oxide be present in an amount effective to impart radiopacity. As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

Oxides of heavy metals having an atomic number greater than about 28 can be preferred. The heavy metal oxide should be chosen such that undesirable colors or shading are not imparted to the hardened resin in which it is dispersed. For example, iron and cobalt would not be favoured, as they impart dark and contrasting colors to the neutral tooth color of the dental material. More preferably, the heavy metal oxide is an oxide of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72 are optionally included in the materials of the invention. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof. The heavy metal oxide particles may be aggregated. If so, it is preferred that the aggregated particles are less than about 200 nm, and more preferably are less than about 90 nm in average diameter.

In a preferred embodiment the filler matrix comprises a nano-sized filler including nano-sized silica.

Preferred nano-sized silicas are commercially available from Nalco Chemical Co. (Naperville, Ill.) under the product designation NALCO COLLOIDAL SILICAS (for example, preferred silica particles can be obtained from using NALCO products 1040, 1042, 1050, 1060, 2327 and 2329), Nissan Chemical America Company, Houston, Tex. (for example, SNOWTEX-ZL, -OL, -O, -N, -C, -20L, -40, and -50); Admatechs Co., Ltd., Japan (for example, SX009-MIE, SX009-MIF, SC1050-MJM, and SC1050-MLV); Grace GmbH & Co. KG, Worms, Germany (for example, those available under the product designation LUDOX, e.g., P-W50, P-W30, P-X30, P-T40 and P-T40AS); Akzo Nobel Chemicals GmbH, Leverkusen, Germany (for example, those available under the product designation LEVASIL, e.g., 50/50%, 100/45%, 200/30%, 200A/30%, 200/40%, 200A/40%, 300/30% and 500/15%), and Bayer MaterialScience AG, Leverkusen, Germany (for example, those available under the product designation DISPERCOLL S, e.g., 5005, 4510, 4020 and 3030). In a preferred embodiment where the hardenable resin employs a cationic initiation system, the starting silica is preferably acidic (such as Nalco 1042).

Surface-treating the nano-sized silica particles before loading into the dental material can provide a stable dispersion in the resin. "Stable", as used herein, means a dental material in which the particles do not agglomerate after standing for a period of time, such as about 24 hours, under standard ambient conditions, e.g. room temperature (about 20 to about 22° C.), atmospheric pressure, and no extreme electromagnetic forces. Preferably, the surface-treatment stabilizes the nano-sized particles so that the particles will be well dispersed in the hardenable resin and results in a substantially homogeneous composition. Furthermore, it is preferred that the silica be modified over at least a portion of its surface with a surface treatment agent so that the stabilized particle can copolymerize or otherwise react with the hardenable resin during curing.

The silica particles can be treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174, available commercially from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, hydroxy alkyl, hydroxy aryl, or amino alkyl functional silanes.

Upon surface treating the silica particles, they can then be combined with an appropriate hardenable resin to form a dental composition of the invention.

The filler matrix can comprise at least about 25 wt.-% or at least about 30 wt.-% or at least about 40 wt.-% or at least about 50 wt.-% of the whole composition.

The amount of filler to be used in the filler matrix usually depends on the purpose for which the composition should be used.

The filler matrix can comprise up to about 90 wt.-% or up to about 85 wt.-% or up to about 80 wt.-% or up to about 75 wt.-% of the whole composition.

Temporary crown and bridge materials (as an example for a dental composition) usually do not contain a high amount of fillers. With respect to these compositions, the filler content usually is in a range of about 30 to about 60 wt.-% with respect to the whole composition.

In dental filling materials (as another example for a dental composition; sometimes also referred to as dental composite materials), which typically contain a higher amount of fillers compared to temporary crown and bridge materials, the filler content is usually in a range of about 60 to about 85 wt.-% with respect to the whole composition.

According to another embodiment the composition may further comprise a further polymerizable component (D) being different from compound (A). Component (D) is typically a free-radically polymerizable material, including ethylenically unsaturated monomer, monomers or oligomers or polymers.

Suitable polymerizable components contain at least one ethylenically unsaturated bond, and are capable of undergoing addition polymerization. Such free-radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, the diurethane dimethacrylate called UDMA (mixture of isomers, e.g. Röhm Plex 6661-0) being the reaction product of 2-hydroxyethyl methacrylate (HEMA) and 2,2,4-trimethylhexamethylene diisocyanate (TMDI), glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate; polyfunctional (meth)acrylates comprising urethane, urea or amide groups, as those of EP 2007111356, herewith incorporated by reference. Mixtures of two or more of these free radically polymerizable materials can be used if desired.

If desired, the polymerizable material(s) may contain both cationically polymerizable and free-radically polymerizable functionalities in a single molecule. These may be obtained, for example, by reacting a di- or poly-epoxide with one or more equivalents of an ethylenically unsaturated carboxylic acid. Examples of such materials include the reaction product of UVR-6105 (available from Union Carbide) or DER 332 (available from Dow Chemical Co.) with one equivalent of methacrylic acid. Commercially available materials having epoxy and free-radically polymerizable functionalities include the "Cyclomer" series, such as Cyclomer M100 or M101, available from Daicel Chemical, Japan.

If present, component (D) is typically present in the composition in an amount of at least about 5 wt.-% or at least about 10 wt.-% or at least about 20 wt.-%.

If present, the amount of component (D) contained in the composition is typically up to about 45 wt.-% or up to about 55 wt.-% or up to about 65 wt.-%.

If present, typical ranges include from about 5 to about 65 or from about 10 to about 55 or from about 10 to about 40 or from about 10 to about 25 wt.-%.

The polymerizable material(s) can also comprise a softener (E) not comprising polymerizable groups.

The softener (E) can comprise hydroxyl functionalities.

Preferably, the hydroxyl group containing material may contain two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e. from about 32 to 200, intermediate molecular weight, i.e. from about 200 to 10,000, or high molecular weight, i.e. above about 10,000. As used herein, all molecular weights are weight average molecular weights.

The hydroxyl group containing material can optionally contain other functionalities that do not substantially interfere with cationic polymerization at room temperature. Thus, the hydroxyl group containing materials can be nonaromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic polymerization at room temperature. The hydroxyl group containing material can, for example, be selected from naturally occurring or synthetically prepared cellulosic materials. Of course, the hydroxyl group containing material is also substantially free of groups that may be thermally or photolytically unstable; that is, the material will not decompose or liberate volatile components at temperatures below about 100° C. or in the presence of actinic light that may be encountered during the desired polymerization conditions for the photo-copolymerizable composition.

Representative examples of suitable hydroxyl group containing materials having a hydroxyl functionality of 1 include alkanols, monoalkyl ethers of polyoxyalkyleneglycols, monoalkyl ethers of alkylene-glycols, and others known in the art.

Representative examples of useful monomeric polyhydroxy organic materials include alkylene glycols (e.g., 1,2-ethanediol; 1,3-propanediol; 1,4-butanediol; 1,6-hexanediol; 1,8-octanediol; 2-ethyl-1,6-hexanediol; bis(hydroxymethyl) cyclohexane; 1,18-dihydroxyoctadecane; 3-chloro-1,2-propanediol); polyhydroxyalkanes (e.g., glycerine, tri-methylolethane, pentaerythritol, sorbitol) and other polyhydroxy compounds such as N,N-bis(hydroxyethyl)benzamide; 2-butyne-1,4-diol; 4,4-bis(hydroxymethyl)diphenylsulfone; castor oil; and the like.

Representative examples of useful polymeric hydroxyl group containing materials include polyoxyethylene and polyoxypropylene glycols, and particularly the polyoxyethylene and polyoxypropylene glycol diols and triols having molecular weights from about 200 to about 10,000 corresponding to a hydroxy equivalent weight of 100 to 5000 for the diols or 70 to 3300 for triols; polytetramethylene ether glycols such as polytetrahydrofuran or "poly THF" of varying molecular weight; copolymers of hydroxypropyl and hydroxyethyl acrylates and methacrylates with other free radical-polymerizable monomers such as acrylate esters, vinyl halides, or styrene; copolymers containing pendent hydroxy groups formed by hydrolysis or partial hydrolysis of vinyl acetate copolymers, polyvinylacetal resins containing pendent hydroxyl groups; modified cellulose polymers such as hydroxyethylated and hydroxypropylated cellulose; hydroxy-terminated polyesters; hydroxy-terminated polylactones, and particularly the polycaprolactones; fluorinated polyoxyethylene or polyoxypropylene glycols; and hydroxy-terminated polyalkadienes.

Useful commercially available hydroxyl group containing materials include the "TERATHANE" series of polytetramethylene ether glycols such as "TERATHANE" 650, 1000, 2000 and 2900 (available from du Pont de Nemours, Wilmington, Del.), polytetrahydrofuran with an average molecular weight of 250 (available from Sigma-Aldrich, St. Louis, Mo.), the "PEP" series of polyoxyalkylene tetrols having secondary hydroxyl groups such as "PEP" 450, 550 and 650; "BUTVAR" series of polyvinylacetal resins such as "BUTVAR" B-72A, B-73, B-76, B-90 and B-98 (available from Monsanto Chemical Company, St. Louis, Mo.); and the "FORMVAR" series of resins such as 7/70, 12/85, 7/95S, 7/95E, 15/95S and 15/95E (available from Monsanto Chemical Company); the "TONE" series of polycaprolactone polyols such as "TONE" 0200, 0210, 0230, 0240, 0300 and 0301 (available from Union Carbide); "PARAPLEX U-148" aliphatic polyester diol (available from Rohm and Haas, Philadelphia, Pa.), the "MULTRON" R series of saturated polyester polyols such as "MULTRON" R-2, R-12A, R-16, R-18, R-38, R-68 and R-74 (available from Mobay Chemical Co.); "KLUCEL E" hydroxypropylated cellulose having an equivalent weight of approximately 100 (available from Hercules Inc.); "Alcohol Soluble Butyrate" cellulose acetate butyrate ester having a hydroxyl equivalent weight of approximately 400 (available from Eastman Kodak Co., Rochester, N.Y.); polyether polyols such as polypropylene glycol diol (e.g., "ARCOL PPG-425", "Arcol PPG-725", "ARCOL PPG-1025", "ARCOL PPG-2025", "ARCOL PPG- 3025", "ARCOL PPG-4025" from ARCO Chemical Co.); polypropylene glycol triol (e.g., "ARCOL LT-28", "ARCOL LHT-42", "ARCOL LHT 112", "ARCOL LHT 240", "ARCOL LG-56", "ARCOL LG-168", "ARCOL LG-650" from ARCO Chemical Co.); ethylene oxide capped polyoxypropylene triol or diol (e.g., "ARCOL 11-27", "ARCOL 11-34", "ARCOL E-351", "ARCOL E-452", "ARCOL E-785", "ARCOL E-786" from ARCO Chemical Co.); ethoxylated bis-phenol A; propylene oxide or ethylene oxide-based polyols (e.g., "VORANOL" polyether polyols from the Dow Chemical Co.).

The amount of hydroxyl group containing organic material optionally used in the compositions of the invention may vary over broad ranges, depending upon factors such as the compatibility of the hydroxyl-containing material with the resin, the equivalent weight and functionality of the hydroxyl-containing material, the physical properties desired in the final cured composition, the desired speed of photopolymerization, and the like.

Blends of various hydroxyl groups containing materials are also contemplated in this invention. Examples of such blends include two or more molecular weight distributions of hydroxyl-containing compounds, such as low molecular weight (below 200), intermediate molecular weight (about 200 to 10,000) and higher molecular weight (above about 10,000). Alternatively or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

If present, component (E) is typically present in the composition in an amount up to about 10 wt.-% or up to about 15 wt.-% or up to about 20 wt.-%.

If present, typical ranges include from about 0 to about 20 wt.-% or from about 0 to about 15 wt.-% or from about 0 to about 10 wt.-%.

The compositions of the invention can also comprise suitable adjuvants such as accelerators, inhibitors or retarders, absorbers, stabilizers, pigments, dyes, surface tension depressants and wetting aids, antioxidants, and other ingredients well known to those skilled in the art.

The amounts and types of each ingredient in the composition should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

Typical adjuvants include pigments, colorants and/or dyes. Examples include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual coloring of the dental compositions.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino) methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers). Such adjuvants may optionally comprise reactive functionality so that they will be copolymerized with the resin.

There is no absolute need for these adjuvants to be present, so adjuvants might not be present at all. However, if they are present they are typically present in an amount of at least about 0.01 wt.-% or at least about 0.5 wt.-% or at least about 1 wt.-% with respect to the whole composition.

The adjuvants can be present in an amount up to about 25 wt.-% or up to about 20 wt.-% or up to about 15 wt.-% with respect to the whole composition.

The composition as described in the text of the invention may comprise the components in the following amounts:
 Compound (A): from about 5 to about 70 or from about 10 to about 60 or from about 10 to about 45 or from about 10 to about 30 wt.-%,
 Initiator (B): from about 0.1 to about 3 or from about 0.2 to about 2 or from about 0.3 to about 1.8 wt.-%,
 Filler (C): from about 0 to about 90 wt.-% or from about 20 to about 85 wt.-% or from about 30 to about 85 wt.-% or from about 40 to about 80 wt.-%,
 Polymerizable compound (D): from about 0 to about 65 or from about 5 to about 55 or from about 10 to about 40 or from about 10 to about 25 wt.-%,
 Softener (E): from about 0 to about 20 wt.-% or from about 0 to about 15 wt.-% or from about 0 to about 10 wt.-%,
 Adjuvant (F): from about 0 to about 25 wt.-% or from about 0.01 to about 20 wt.-% or from about 0.5 to about 15 wt.-%.
wt.-% with respect to the weight of the whole composition.

The curable composition of the invention can be obtained by combining (including mixing and kneading) the individual components of the composition, preferably under "safe light" conditions.

Suitable inert solvents may be employed if desired when providing the mixture. Any solvent may be used which does not react appreciably with the components of the inventive compositions. Examples of suitable solvents include acetone, dichloromethane, acetonitrile and lactones. A liquid material to be polymerized may be used as a solvent for another liquid or solid material to be polymerized. If desired, the solvents can be removed after the composition has been produced.

Thus, according to one embodiment the invention is also directed to a process for producing the composition, wherein the process comprises a mixing step, where the components being present in the composition are mixed, Compound (A) as described in the present text is obtainable according to either of the following methods:
 A) by reacting
  a component comprising a tricyclic hydrocarbon moiety bearing at least two OH moieties with
  a component represented by the formula (MA)-(SU)-NCO,
  with (MA) being methacrylate or acrylate, (SU) being a non-branched spacer unit comprising at least about 3 carbon atoms, and NCO being an isocyanate moiety
 or
 B) by reacting
  a component comprising a tricyclic hydrocarbon moiety bearing at least two OH moieties with an urethane moiety forming activating agent,
followed by reaction with (MA)-(SU)-Y$^+$X$^-$
with (MA) being methacrylate or acrylate, (SU) being a non-branched spacer unit comprising at least about 3 carbon atoms, X being selected from tosylate, mesylate, trifluoroacetate and Y being selected from ammonium.

If desired, completion of the reaction (i.e. production of compound (A)) can be determined by IR spectroscopy, especially focussing on the NCO band showing an absorption band at about 2273 cm$^{-1}$.

The reaction can typically be carried out in a temperature range of about 40 to about 110° C., preferably under dry conditions (e.g. dry air). The reaction can be carried out in common solvents (including hexane, cyclohexane, methylcyclohexane, toluene, ethyl acetate, diethylether, methyl-tert-butyl-ether, tetrahydrofurane) or without a solvent.

To prevent unwanted radical polymerization during the synthesis, a stabilizer in an appropriate amount (e.g. 50 to 500 ppm) such as 3,5-di-tert.-butyl-4-hydroxy-toluene (BHT), 4-methoxyphenol (MOP), or hydroquinone (HQ) can be used, but is not mandatory.

If desired, compound (A) can be combined with surface treated SiO$_2$ and/or ZrO$_2$ nano particles to obtain dispersions of surface treated SiO$_2$ and/or ZrO$_2$ nano particles within compound (A).

If desired, further details of the respective conditions for producing compound (A) can be taken from the Examples below.

Examples of (MA)-(SU)-NCO include 3-isocyanatopropyl methacrylate (IProM), 3-isocyanatopropyl acrylate (IPrA), 5-isocyanatopentyl methacrylate (IPM), 5-isocyanatopentyl acrylate (IPA), and mixtures thereof.

Examples of component comprising a tricyclic hydrocarbon moiety bearing at least two OH moieties include TCD alcohol.

Examples of an urethane moiety forming activating agent include Carbonyl-diimidazol (CDI), Phosgene and mixtures thereof.

Examples of (MA)-(SU)-Y$^+$X$^-$ include 3-Methacroyloxypropyl-ammonium Tosylate (MAPrA-TS), 3-Acroyloxypropyl-ammonium Tosylate (APrA-TS), 5-Methacroyloxypentyl-ammonium Tosylate (MAPA-TS) or 5-Acroyloxypentyl-ammonium Tosylate (APA-TS), and mixtures thereof.

The invention provides a composition which can be hardened in an acceptable time frame, e.g., less than about 120 seconds (s) or less than about 100 s or less than about 60 s, and to a sufficient depth. Depending on the initiator system used, a visible light source equipment already available in the dental office or electronics fabrication facilities can be used to initiate the hardening reaction.

The compositions of the invention are particularly well adapted for use as a wide variety of dental materials, which may be filled or unfilled. Such dental materials include (direct aesthetic) restorative materials (e.g., anterior and posterior restoratives), prostheses, adhesives for oral hard tissues, sealants, veneers, cavity liners, orthodontic bracket adhesives for use with any type of bracket (such as metal, plastic and ceramic), crown and bridge cements, artificial crowns, artificial teeth, dentures, and the like.

These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth. The term "sealant" as used herein refers to a lightly filled dental composite that is cured after it is disposed adjacent to a tooth.

When the dental material is applied to a tooth, the tooth can optionally be pre-treated with a primer such as dentin or enamel adhesive by methods known to those skilled in the art.

The compositions of the invention can be used e.g. for producing either of the following materials: artificial crown, (anterior or posterior) filling material, casting material, cavity liner, cement, coating composition, mill blank, orthodontic device, restorative, prosthese and sealant.

In a preferred aspect, the dental material is a dental filling material. The dental filling materials of the invention can be placed directly in the mouth and cured (hardened) in situ, or alternatively, may be fabricated into a prosthesis outside the mouth and subsequently adhered in place inside the mouth.

The invention is also directed to a process for treating a tooth, the process comprising the steps of:
a) placing the composition comprising compound (A) in contact with a tooth,
b) hardening the composition.

The inventive dental composition is typically stored in a container until use. Depending on the initiator system chosen, various containers can be suitable.

If the dental composition is provided as a one-component system, it can be stored in a container having only one chamber such as a compule. The compule has typically a cylindrical housing with a front and a rear end and a nozzle. The rear end of the housing is usually sealed with a movable piston. Typically, the dental composition is dispensed out of the compule or container using an applier having a movable plunger (e.g. an application device having the shape of a caulk gun). Examples of suitable compules or containers are described in U.S. Pat. No. 5,624,260, EP 1 340 472 A1, US 2007/0172789 A1, U.S. Pat. No. 5,893,714 and U.S. Pat. No. 5,865,803, the content of which with regard to the description of compules or containers is herewith incorporated by reference.

Alternatively, if the dental composition is provided as a two-component system, it can be stored in a dual-chamber container or cartridge and is mixed before use.

Cartridges which can be used are described e.g. in US 2007/0090079 or U.S. Pat. No. 5,918,772, the disclosure of which is incorporated by reference. Cartridges which can be used are commercially available from SulzerMixpac AG (Switzerland).

Static mixing tips which can be used are described e.g. in US 2006/0187752 or in U.S. Pat. No. 5,944,419, the disclosure of which is incorporated by reference. Mixing tips which can be used are commercially available from SulzerMixpac AG (Switzerland).

Thus, another embodiment of the invention is directed to a kit of parts comprising at least two, three, four, five, six or more compositions differing from each other at least with respect to their colour. As outlined above, the compositions are typically stored in a container.

The container may comprise a housing having a front end with a nozzle and a rear end and at least one piston movable in the housing.

The volume of the container is typically in the range from about 0.1 to about 100 ml or from about 0.5 to about 50 ml or from about 1 to about 30 ml.

Certain embodiments of the invention are essentially free from low boiling solvents (e.g. boiling point below about 150° C. at ambient pressure). In this context "essentially free from" means that the content is typically below about 1 wt.-% or below about 0.5 wt.-% or below about 0.1 wt.-% with respect to the whole composition.

The complete disclosures of the patents, patent documents, and publications cited herein are incorporated by reference in their entirety as if each were individually incorporated. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

EXAMPLES

Unless otherwise indicated, all parts and percentages are on a weight basis, all water is deionized water, and all molecular weights are weight average molecular weight. Moreover, unless otherwise indicated all Experiments were conducted at ambient conditions (23° C.; 1013 mbar). Moreover, nearly all process steps are conducted under an atmosphere of dry air:

Compressive Strength (CS)

6 specimens of each material were be prepared and the measurements was carried out according to ISO 9917 using a universal testing machine (Zwick Z 010), with the proviso that test specimens having the dimension of 3 mm×3 mm×5 mm were used in combination with a crosshead speed of 4 mm/min. The compressive strength is given in [MPa].

Flexural Strength (FS)

The measurement of the flexural strength was carried out according to ISO 4049 using a universal testing machine (Zwick Z 010, crosshead speed 1 mm/min). The flexural strength is given in MPa.

E-Modulus (E.-M.)

The E-M (I) was determined according to ISO 4049 and is given in [GPa].

Bonded Disk Shrinkage-Strain (SHR)

The Bonded Disk Shrinkage-Strain was determined according to the Watts protocol as described in more detail in Dent. Mater. 1991, 7, 281-287. Unit: [%].

Depth of Cure (DoC)

Depth of cure (i.e., cure depth) was analyzed according to ISO 4049 by packing a paste sample into a cylindrical metal curing mould (8 mm deep, 4 mm diameter) and curing the sample for 40 s with an ELIPAR™ Trilight Standard (800 mW/cm2) (3M ESPE Company). The cured sample was removed from the mould and uncured paste was scraped off of the sample with a plastic applicator after less than about one minute of curing. Results are reported as the average of three replicates.

Refractive Index ($n_D^{20}$)

The refractive index was measured with a Kruess AR 4 D device (refractometer according to Abbe's measure principle). The refractive index was measured at 20.0° C. at a wavelength of 589 nm.

Viscosity ($\eta$)

The viscosity was measured with a Haake RotoVisco RV1 device (rotor C60/1 for viscosities up to 8000 mPas or rotor C20/1 for viscosities above 8000 mPas together with stator P61). The viscosity was measured at 23.0° C. between two plane and parallel plates (i.e. stator and rotor). After activation and rectification of the system, the appropriate rotor was installed. Then the rotor was lowered and the distance between stator and rotor was adjusted to 0.052 mm (using Software RheoWin Pro Job Manager Software Version 2.94) for the viscosity measurement. Then the rotor was lifted and the material to be measured was given onto the stator (1.0 ml with rotor C60/1 or 0.04 ml with rotor C20/1). Without undue delay, the rotor was lowered into the preliminary adjusted measuring position. The material to be measured was tempered at 23.0° C. The shear rate for the measurement has to be adjusted to a value that the torque is at least 5000 μNm (therefore normally shear rates of 100, 200, 500, or 1000 $s^{-1}$ are used depending on the viscosity of the material to be measured). The measurement was started and run for 60 s. The viscosity values (Pas) were recorded starting 20 s after the start of measurement and the mean value of the recorded values is given as viscosity.

Shrinkage Stress (Stress)

Shrinkage stress was measured according to the procedure of Sakaguchi et al. (Dent. Mater. 1997, 13, 233-239). Irradiation of 45 mg samples was done for 40 s using a 3M XL3000 (650 mW) irradiation device. The stress value in μstrain was recorded 10 min after start of the irradiation.

Compositions

Abbreviations

The name and/or structure of the components used are given in Table 1.

TABLE 1

| Abbreviation | Description | Source | Component |
|---|---|---|---|
| APrA-TS | 3-Acroyloxypropyl-ammonium Tosylate | | |
| ABA-TS | 4-Acroyloxybutyl-ammonium Tosylate | | |
| APA-TS | 5-Acroyloxypentyl-ammonium Tosylate | | |
| BHT | 2,6-Di-tert-butyl-4-methylphenol, 2,6-Di-tert-butyl-p-cresol, 3,5-Di-tert-butyl-4-hydroxytoluene (CAS no. 7637-07-2) | | |
| CDI | Carbonyl-diimidazol (CAS no. ) | | |
| CPQ | Camphorquinone (CAS no. 10373-78-1) | | g) |
| DPI-PF6 | Diphenyliodonium hexafluorophosphate (CAS no. 58109-40-3) | | h) |
| EDMAB | Ethyl 4-dimethylaminobenzoate (CAS no. 10287-53-3) | | i) |
| Filler | Spray dried zirconia silica filler, <1 μm, surface treated | | j) |
| HQME | Hydroquinone methyl ether (CAS no. 150-76-5) | | |
| IEM | 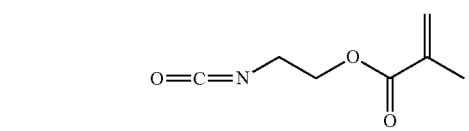 | | |

2-Isocyanatoethyl methacrylate, 2-Methacroyloxyethyl isocyanate (CAS no. 30674-80-7); Mw = 155.15

TABLE 1-continued

| Abbreviation | Description | Source | Component |
|---|---|---|---|
| IEA | 2-Isocyanatoethyl acrylate, 2-Acroyloxyethyl isocyanate (CAS no. 13641-96-8); Mw = 141.12 | | |
| IProM | 3-Isocyanatopropyl methacrylate, 3-Methacroyloxypropyl isocyanate; Mw = 169.18 | | |
| IPrA | 3-Isocyanatopropyl acrylate, 3-Acroyloxypropyl isocyanate Mw = 155.15 | | |
| IBM | 4-Isocyanatobutyl methacrylate, 4-Methacroyloxybutyl isocyanate Mw = 183.21 | | |
| IBA | 4-Isocyanatobutyl acrylate, 4-Acroyloxybutyl isocyanate; Mw = 169.18 | | |
| IPM | 5-Isocyanatopentyl methacrylate, 5-Methacroyloxypentyl isocyanate; Mw = 197.24 | | |
| IPA | 5-Isocyanatopentyl acrylate, 5-Acroyloxypentyl isocyanate Mw = 183.21 | | |
| MAPrA-TS | 3-Methacroyloxypropyl-ammonium Tosylate | | |
| MABA-TS | 4-Methacroyloxybutyl-ammonium Tosylate | | |
| MAPA-TS | 5-Methacroyloxypentyl-ammonium Tosylate | | |
| TCD alcohol | 3/4,8/9-Tricyclo[5.2.1.0$^{2,6}$]decane dimethanol, mixture of isomers (CAS no. 26896-48-0); Mw = 196.3 | | |

TABLE 1-continued
| Abbreviation | Description | Source | Component |
|---|---|---|---|
| T-IEM | TCD-Alcohol - IEM, reaction product of tricyclo[5.2.1.02,6]decane dimethanole (TCD-Alcohol DM) and IEM | C.E. 1 | a) |
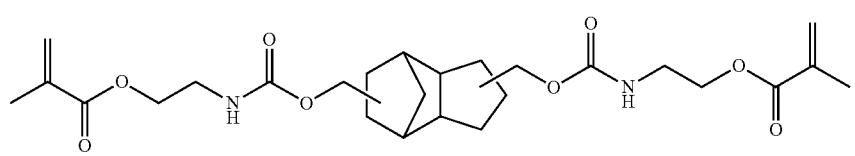
Mw = 506.6; $n_D^{20}$ = 1.510; η = 1100 Pa*s
T2EO-IEM        C.E. 2   b)
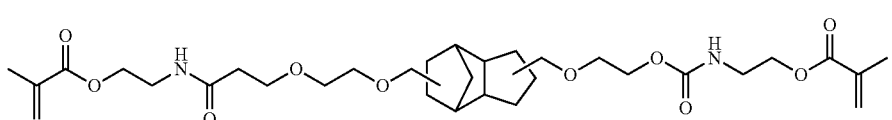
Mw = 594.7; $n_D^{20}$ = 1.503; η = 90 Pa*s
T3EO-IEM        C.E. 3   c)
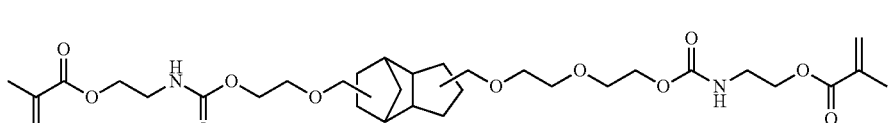
Mw = 638.8; $n_D^{20}$ = 1.499; η = 40 Pa*s
TCDI-HEA        C.E. 4   d)
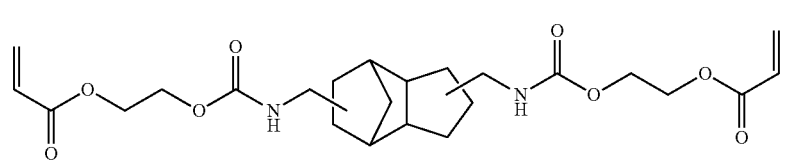
Mw = 478.5; $n_D^{20}$ = 1.508; η = 1200 Pa*s
T-IProM        E1   e)
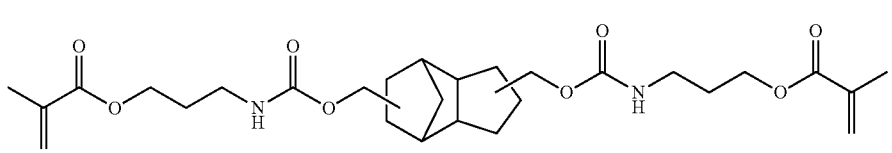
Mw = 534.6; $n_D^{20}$ = 1.508; η = 112 Pa*s
T-IPrA
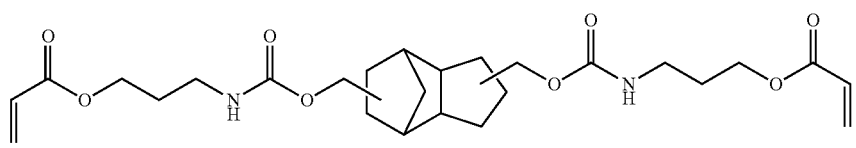
Mw = 506.6
T-IBM
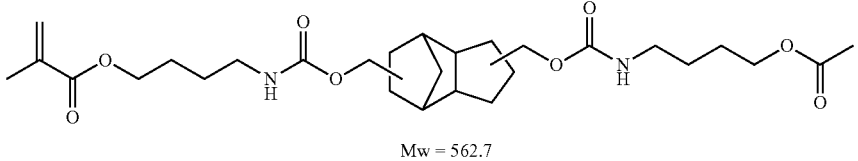
Mw = 562.7
T-IBA
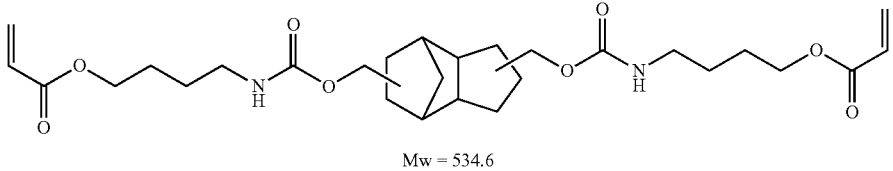
Mw = 534.6

TABLE 1-continued

| Abbreviation | Description | Source | Component |
|---|---|---|---|
| T-IPM | [structure] Mw = 590.8; $n_D^{20}$ = 1.504; η = 25 Pa*s | E2 | f) |
| T-IPA | [structure] Mw = 562.7 | | |

Synthesis Compound (A)

Compound(s) (A) can be prepared as follows:
General Procedure 1: One Step Reaction of TCD-Alcohol with an Isocyanato Functional (Meth)Acrylate Building Block (e.g. IEM)

To TCD-Alkohol 200-640 ppm of BHT and 100 ppm of bismuth neodecanoate (Bi-Cat, 20 wt.-% of bismuth, 100 ppm with respect to the amount of bismuth alone) are added. At a temperature of about 50° C. e.g. IEM is added while stirring so that the temperature does not exceed about 55° C. After completion of the addition the reaction mixture is stirred for at least additional about 16 hours at a temperature of about 50° C. until completion of the addition reaction (measured via FTIR: the corrected height of the NCO band at about 2270 $cm^{-1}$ is below 0.05).

General Procedure 2: Synthesis of an Ammonium Functional (Meth)Acrylate Building Block (e.g. MAPrA-TS)

Out of a mixture of para-toluene sulfonic acid monohydrate (HOTos), e.g. 3-aminopropan-1-ole, and methacrylic acid (MA) in toluene water is stripped off using a Dean-Starck apparatus. After completion of the reaction the product (e.g. MAPrA-TS) crystallizes during cooling. The precipitate is separated by filtration, washed with toluene, and dryed in vacuo.

To a solution of TCD-Alcohol in toluene 1,1-Carbonyldiimidazolide (CDI) is added and the resulting mixture is stirred over night. Orthophosphoric acid is added and the colorless precipitate of imidazolium dihydrogenphosphate is removed by filtration. To the filtrate (a solution of the diimidazolide of TCD-Alcohol) 500-2000 ppm of HQME, 200-1000 ppm of BHT, and e.g. MAPrA-TS are added. The resulting mixture is stirred over night at a temperature of about 80° C. At room temperature the colorless precipitate of imidazolium tosylate is removed by filtration. The filtrate is subsequently extracted with phosphoric acid, sodium hydroxide solution, phosphoric acid, and water. After stirring over night with charcoal and filtration through acidic alumina 100-500 ppm of HQME and 100-500 ppm of BHT are added to the filtrate and the solvent is stripped off in vacuo while bubbling air through the crude product.

Synthesis of T-IEM

Comparative Example 1

According to General Procedure 1 42.5 g of TCD alcohol and 66.5 g of IEM were reacted. 97.7 g of T-IEM (193 mmol, 90%) were isolated as yellow oil: η=1100 Pa*s, $n_D^{20}$=1.510.

Synthesis of T2EO-IEM

Comparative Example 2

According to General Procedure 1 35.3 g of TCD alcohol Ethoxylate (2 EO per TCD Alkohol, T2EO) and 40.3 g of IEM were reacted. 73.4 g of T2EO-IEM (123 mmol, 97%) were isolated as brownish oil: η=90 Pa*s, $n_D^{20}$=1.503.

Synthesis of T3EO-IEM

Comparative Example 3

According to General Procedure 1 35.0 g of TCD alcohol Ethoxylate (3 EO per TCD Alkohol, T3EO) and 35.0 g of IEM were reacted. 68.0 g of T3EO-IEM (106 mmol, 97%) were isolated as brownish oil: η=40 Pa*s, $n_D^{20}$=1.499.

Synthesis of T-IProM

Inventive Example 1

According to General Procedure 1 15.0 g of TCD alcohol and 25.6 g of IProM were reacted. 35.5 g of T-IProM (66.4 mmol, 87%) were isolated as yellowish oil: η=112 Pa*s, $n_D^{20}$=1.508.

Alternative Synthesis of T-IProM

Inventive Example 1, Alternative Preparation

According to General Procedure 3 50.4 g of TCD alcohol, 83.4 g of CDI, 60.0 g of orthophosphoric acid, and 170 g of MAPrA-Ts were reacted in 500 ml of ethylacetate. 97.0 g of T-IProM (181 mmol, 70%) were isolated as yellowish oil: η=109 Pa*s, $n_D^{20}$=1.508.

Synthesis of T-IPM

Inventive Example 2

According to General Procedure 1 15.6 g of TCD alcohol and 30.9 g of IPM were reacted. 44.1 g of T-IPM (74.6 mmol, 95%) were isolated as yellowish oil: η=25 Pa*s, $n_D^{20}$=1.504.

Alternative Synthesis of T-IPM

Inventive Example 2, Alternative Preparation

According to General Procedure 3 60.0 g of TCD alcohol, 99.1 g of CDI, 70.5 g of orthophosphoric acid, and 220 g of MAPA-TS were reacted in 500 ml of ethylacetate. 114 g of T-IPM (193 mmol, 63%) were isolated as yellowish oil: η=25 Pa*s, $n_D^{20}$=1.504.

Synthesis Compositions

Some of the compounds synthesized were used for producing a (dental) composition.

The compositions produced and tested with respect to their mechanical properties are given in Table 2 below. In Table 2 the values of the components a) to s) represent %-weight of the individual components in the corresponding dental formulation.

General Procedure A:

With magnetic stirring and under the exclusion of light the initiator system components were dissolved within the monomers at temperatures not above 50° C. (depending on the intrinsic viscosity of the used monomers).

General Procedure B:

According to General Procedure A the initiator system components were dissolved within the monomers. Under the exclusion of light and using a two-arm kneader the filler was mixed in portions with this mixture of initiator system and monomers. The amount of filler was manually determined depending on the desired handling properties of the dental composition. The dental composition was then light cured using a 800 mW halogen curing light (3M ESPE Elipar™ Trilight) and tested according to the corresponding measurements listed above. The respective values are given in Table 2.

TABLE 2

| | Dental Composition | | | | | |
|---|---|---|---|---|---|---|
| | A CE 1 | B CE 2 | C CE 3 | D CE 4 | E | F |
| a) | 21.0 | | | | | |
| b) | | 19.7 | | | | |
| c) | | | 19.5 | | | |
| d) | | | | 20.8 | | |
| e) | | | | | 18.9 | |
| f) | | | | | | 18.0 |
| g) | 0.03 | 0.03 | 0.03 | 0.03 | 0.03 | 0.03 |
| h) | 0.19 | 0.19 | 0.19 | 0.19 | 0.19 | 0.19 |
| i) | 0.09 | 0.09 | 0.09 | 0.09 | 0.09 | 0.09 |
| j) | 78.7 | 80.0 | 80.2 | 78.9 | 80.8 | 81.7 |
| CS [MPa] | 277 | 379 | 406 | 224 | 380 | 389 |
| FS [MPa] | 109 | 168 | 163 | 65 | 145 | 144 |
| E-M. [GPa] | 10.4 | 10.7 | 10.8 | 2.00 | 13.0 | 11.0 |
| DoC [mm] | 4.13 | 2.28 | 2.46 | 2.73 | 4.75 | 4.26 |

TABLE 2-continued

| | Dental Composition | | | | | |
|---|---|---|---|---|---|---|
| | A CE 1 | B CE 2 | C CE 3 | D CE 4 | E | F |
| SHR [%] | 1.40 | 1.49 | 1.63 | 1.27 | 1.38 | 1.33 |
| Stress [µstrain] | 1240 | 1559 | 1614 | 1205 | 1179 | 1229 |

As can be seen, the compositions containing the compound (A) according to the invention are superior compared to compositions containing polymerizable compounds according to the state of the art, i.a. if the values for DoC and Stress are taken into account.

The invention claimed is:

1. A composition comprising
    a) compound (A) being characterized by at least the following features:
        comprising a backbone unit (U) comprising a tricyclodecane moiety,
        two spacer units (S) each comprising a hydrocarbon chain (G) being directly connected to the backbone unit (U) via an urethane moiety, wherein the urethane moiety is connected to the backbone unit (U) through the oxygen, and
        at least two reactive groups (M) being connected to the hydrocarbon chain (G) via an ester linkage,
        with
        (G) being a non-branched hydrocarbon chain selected from C3 to C8 alkylene moieties, (G) not comprising ether moieties and
        (M) being selected from acroyl and methacroyl,
    b) initiator (B) and
    c) filler (C),
the composition being a dental composition, and being characterized by a Shrinkage Stress of below 1350 µstrain, and a Compressive Strength of at least 320 MPa.

2. The composition according to claim 1, compound (A) being characterized by at least one of the following features:
    Molecular weight (Mw): from about 500 to about 600,
    Functionality: 2 reactive groups per molecule,
    Number of urethane moieties: 2;
    Number of ester moieties: 2
    Viscosity: below about 200 Pa*s (measured at 23° C.).

3. The composition according to claim 1 not comprising moieties selected from epoxy, bisphenol, halogen and combinations thereof.

4. The composition according to claim 1, compound (A) being selected from

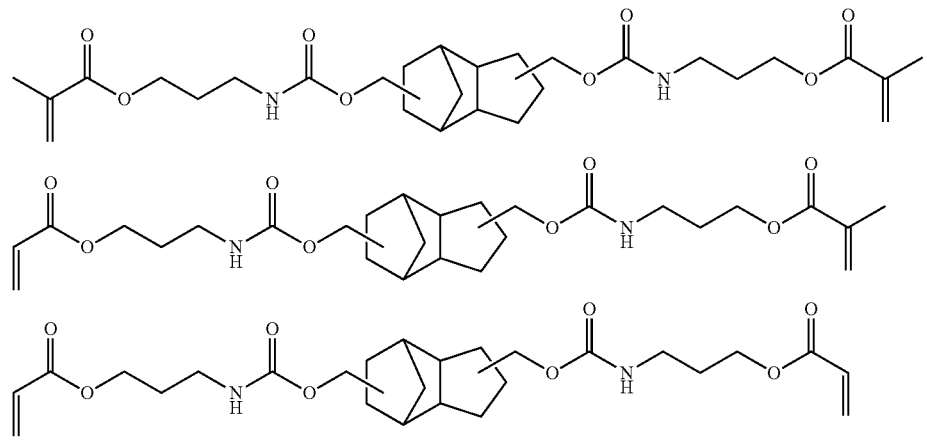

-continued

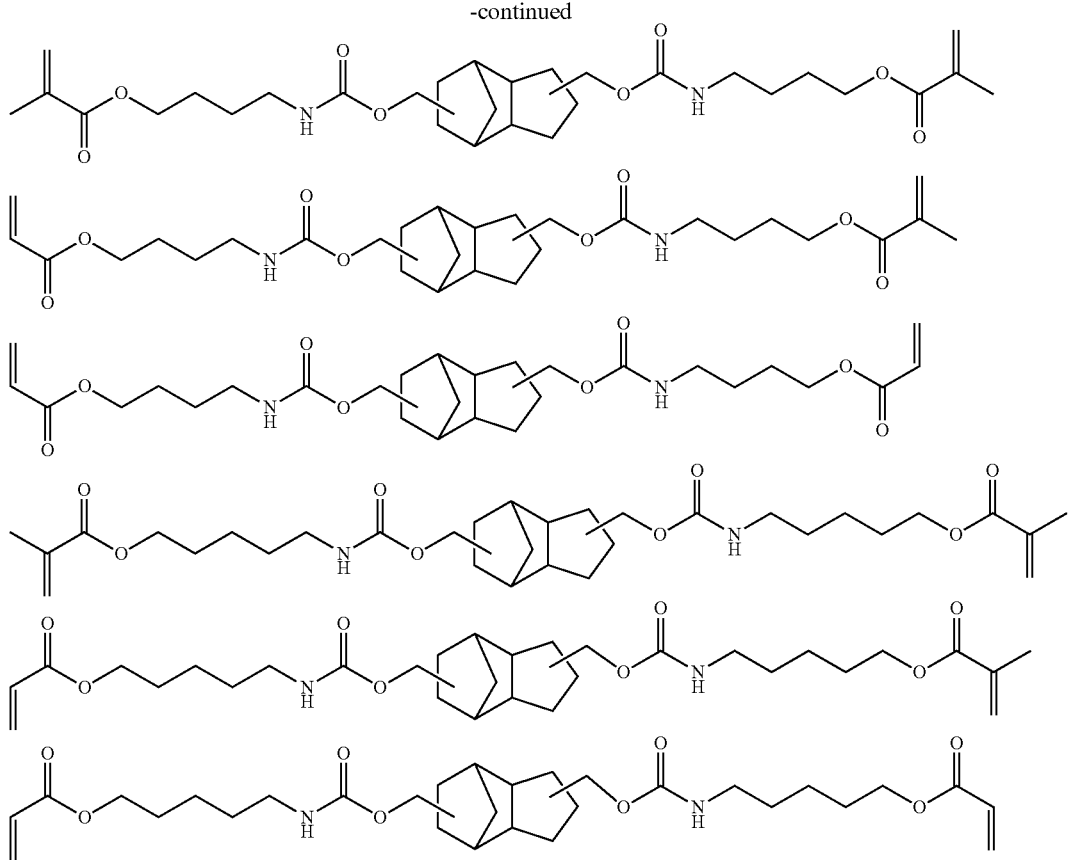

and mixtures thereof.

5. The composition according to claim 1, initiator (B) being a redox initiator, a photo initiator or a combinations or mixture of both.

6. The composition according to claim 1, comprising in addition one or more of the following components:
polymerizable compound (D) being different from compound (A)
softener (E) not comprising polymerizable group(s),
adjuvents (F).

7. The composition according to claim 6, the polymerizable compound (D) being selected from ethylenically unsaturated monomers, oligomers or polymers, combinations and mixtures thereof.

8. The composition according to claim 1 comprising the components in the following amounts:
Compound (A): from about 5 to about 70 wt.-%,
Initiator (B): from about 0.1 to about 3 wt.-%,
Filler (C): from about 0 to about 90 wt.-%,
Polymerizable compound (D): from about 0 to about 65 wt.-%,
Softener (E): from about 0 to about 20 wt.-%,
Adjuvant (F): from about 0 to about 25 wt.-%,
wt.-% with respect to the weight of the whole composition.

9. The composition according to claim 1 being hardenable within about 30 min at a temperature below about 50° C.

10. The composition according to claim 1 being characterized by at least one of the following parameters after hardening:
Flexural strength: at least 120 MPa,
E-Modulus: at least 10 GPa but not higher than 14 GPa,
Depth of Cure: at least 4.2 mm.

11. The composition according to claim 1 being contained in a container.

12. A kit of parts comprising at least 2 compositions as described in claim 1, the compositions differing from each other at least with respect to their colour.

13. A method of using the composition as described in claim 1 for producing a dental cement, a crown and bridge material, a dental filling material, a casting material, a cavity liner, a coating composition, a mill blank, an orthodontic device, a sealant or combinations thereof.

14. A process of producing a composition as described in claim 1 wherein compound (A) is obtained either
by reacting
a component comprising a tricyclic hydrocarbon moiety bearing at least two OH moieties with
a component represented by the formula (MA)-(SU)-NCO,
with (MA) being methacrylate or acrylate, (SU) being a non-branched spacer unit comprising at least about 3 carbon atoms, and NCO being an isocyanate moiety
or
by reacting
a component comprising a tricyclo decane moiety bearing at least two OH moieties with
an urethane moiety forming activating agent,
followed by reaction with (MA)-(SU)-$Y^+X^-$
with (MA) being methacrylate or acrylate, (SU) being a non-branched spacer unit comprising C3 to C8 alkylene moieties, X being selected from tosylate, mesylate, trifluoroacetate and Y being selected from ammonium.

15. A composition comprising
a) compound (A) being characterized by at least the following features:
   comprising a backbone unit (U) comprising a tricyclodecane moiety,
   two spacer units (S) each comprising a hydrocarbon chain (G) being directly connected to the backbone unit (U) via an urethane moiety, wherein the urethane moiety is connected to the backbone unit (U) through the oxygen, and
   at least two reactive groups (M) being connected to the hydrocarbon chain (G) via an ester linkage,
   with
   (G) being a non-branched hydrocarbon chain selected from C3 to C8 alkylene moieties, (G) not comprising ether moieties and
   (M) being selected from acroyl and methacroyl,
b) initiator (B) and
c) filler (C),
the composition being a dental composition.

* * * * *

UNITED STATES PATENT AND TRADEMARK OFFICE
CERTIFICATE OF CORRECTION

| | |
|---|---|
| PATENT NO. | : 9,173,820 B2 |
| APPLICATION NO. | : 14/237210 |
| DATED | : November 3, 2015 |
| INVENTOR(S) | : Adrian Eckert |

It is certified that error appears in the above-identified patent and that said Letters Patent is hereby corrected as shown below:

Title page

Item (57) (Abstract)

Lines 3-4, delete "tricylclic" and insert -- tricyclic --, therefor.

Specification

Column 1

Line 1, delete "i.a." and insert -- i.e. --, therefor.

Column 3

Line 17, delete "i.a." and insert -- i.e. --, therefor.

Column 5

Line 25, delete "dimethanole)" and insert -- dimethanol) --, therefor.

Column 8

Line 28, delete "photoinitator" and insert -- photoinitiator --, therefor.

Column 8

Line 30, delete "(i e.," and insert -- (i.e., --, therefor.

Column 9

Line 15, delete "ACO(X)$_b$B," and insert -- ACO(X)$_b$ B, --, therefor.

Signed and Sealed this
Fifth Day of July, 2016

Michelle K. Lee
*Director of the United States Patent and Trademark Office*

Specification

Column 9

Line 19, delete "or or" and insert -- or --, therefor.

Column 9

Lines 42-43, delete "acenaphthaquinone," and insert -- acenaphthoquinone, --, therefor.

Column 10

Line 59, delete "Safranine O," and insert -- Safranin O, --, therefor.

Column 11

Lines 46-47, delete "quarternary" and insert -- quaternary --, therefor.

Column 15

Line 2, delete "hexacrylate," and insert -- hexaacrylate, --, therefor.

Column 17

Lines 57-58, delete "Neazopon" and insert -- Neozapon --, therefor.

Column 19

Line 17, delete "tetrahydrofurane)" and insert -- tetrahydrofuran) --, therefor.

Column 19

Line 38, delete "diimidazol" and insert -- diimidazole --, therefor.

Column 26 (Table 1)

Line 1, delete "dimethanole)" and insert -- dimethanol) --, therefor.

Column 30

Line 13, delete "i.a." and insert -- i.e. --, therefor.